(12) United States Patent
DeAth

(10) Patent No.: US 7,465,697 B1
(45) Date of Patent: Dec. 16, 2008

(54) ESSENTIAL OILS BASED CLEANING AND DISINFECTING COMPOSITIONS

(75) Inventor: S. Samuel DeAth, Waterdown (CA)

(73) Assignee: Ohsoclean, Inc., San Francisco, CA (US)

( * ) Notice: Subject to any disclaimer, the term of this patent is extended or adjusted under 35 U.S.C. 154(b) by 0 days.

(21) Appl. No.: 11/555,875

(22) Filed: Nov. 2, 2006

(51) Int. Cl.
*C11D 3/50* (2006.01)
*C11D 1/12* (2006.01)
*C11D 7/10* (2006.01)

(52) U.S. Cl. .................. 510/138; 510/130; 510/131; 510/132; 510/156; 510/199; 510/382; 510/390; 510/426; 510/463; 510/101

(58) Field of Classification Search .................. 510/130, 510/131, 132, 138, 156, 199, 382, 390, 426, 510/463, 101
See application file for complete search history.

(56) References Cited

U.S. PATENT DOCUMENTS

| | | | |
|---|---|---|---|
| 3,697,641 | A | 10/1972 | Ahrens |
| 4,411,813 | A | 10/1983 | Voisin |
| 4,748,279 | A | 5/1988 | Whiteley |
| 4,952,398 | A | 8/1990 | Tapin |
| 5,094,842 | A | 3/1992 | Riley |
| 5,145,665 | A | 9/1992 | Klueppel et al. |
| 5,298,238 | A | 3/1994 | Hussein et al. |
| 5,403,587 | A | 4/1995 | McCue et al. |
| 5,437,858 | A | 8/1995 | Hungerbach et al. |
| 5,716,920 | A | 2/1998 | Glenn, Jr. et al. |
| 5,731,281 | A * | 3/1998 | Mondin et al. .............. 510/417 |
| 5,965,518 | A | 10/1999 | Nakatsu et al. |
| 6,010,933 | A | 1/2000 | Cherng |
| 6,010,993 | A | 1/2000 | Romano et al. |
| 6,022,459 | A | 2/2000 | Briggs |
| 6,048,836 | A | 4/2000 | Romano et al. |
| 6,106,838 | A | 8/2000 | Nitsas |
| 6,183,757 | B1 | 2/2001 | Beerse et al. |
| 6,183,763 | B1 | 2/2001 | Beerse et al. |
| 6,197,288 | B1 | 3/2001 | Mankoo |
| 6,210,695 | B1 | 4/2001 | Beerse et al. |
| 6,217,887 | B1 | 4/2001 | Beerse et al. |
| 6,255,268 | B1 | 7/2001 | Counts |
| 6,346,281 | B1 | 2/2002 | DeAth et al. |
| 6,585,961 | B1 | 7/2003 | Stockel |
| 6,613,728 | B1 | 9/2003 | Sirianni et al. |
| 6,649,660 | B2 | 11/2003 | Ninkov |
| 6,753,305 | B2 | 6/2004 | Raso et al. |
| 6,844,369 | B2 | 1/2005 | Ninkov |
| 6,846,498 | B2 | 1/2005 | DeAth et al. |
| 6,884,763 | B2 | 4/2005 | Willard et al. |
| 7,208,519 | B2 | 4/2007 | Ninkov |
| 2004/0057922 | A1 | 3/2004 | Schmid et al. |
| 2004/0247664 | A1 * | 12/2004 | Dreja et al. .................. 424/452 |
| 2005/0137109 | A1 | 6/2005 | Quan et al. |
| 2005/0256018 | A1 | 11/2005 | Keller et al. |
| 2006/0024248 | A1 | 2/2006 | Spengler et al. |
| 2007/0281039 | A1 | 12/2007 | DeAth |

FOREIGN PATENT DOCUMENTS

| | | |
|---|---|---|
| CH | 688 787 | 3/1998 |
| EP | 0842606 | 5/1998 |
| EP | 1 294 373 | 3/2003 |
| EP | 1278420 | 12/2005 |
| FR | 2599026 | 5/1986 |
| JP | 04321628 | 11/1992 |
| WO | WO 94/18939 | 9/1994 |
| WO | WO 96/11694 | 4/1996 |
| WO | WO 97/31093 | 8/1997 |

OTHER PUBLICATIONS

English Abstract of JP Application No. 04207359, Publication No. 06024952, Jan. 2, 1994, Patent Abstracts of Japan, European Patent Office.
Kurt Schnaubelt, Ph.D., Advanced Aromatherapy: The essential oil therapy, Healing Arts Press, Cologne, Germany, pp. 31-41, 1998.
Julia Lawless, The Illustrated Encyclopedia of Essential Oils; The complete guide to the use of oils in aromatherapy and herbalism, Element Books Limited, pp. 132, 139-141 and 228, 1996.
Official Action, issued in related U.S. Appl. No. 11/444,367, mailed Oct. 16, 2006.
Official Action, issued in related U.S. Appl. No. 11/444,367, mailed Dec. 13, 2006.
Official Action, issued in related U.S. Appl. No. 11/444,367, mailed Jun. 25, 2007.
Official Action, issued in related U.S. Appl. No. 11/444,367, mailed Jan. 3, 2008.

* cited by examiner

*Primary Examiner*—Charles I Boyer

(57) ABSTRACT

The present invention provides cleaning and disinfecting compositions for cleaning, disinfecting and sanitizing inanimate and animate surfaces. The cleaning and disinfecting compositions contain thyme oil or thyme oil and *origanum* oil, a salt of a transition metal, sodium dioctyl sulfosuccinate and water. The cleaning and disinfecting compositions of the present invention are surprisingly stable and as such, they may be provided to consumers in the undiluted state. The cleaning and disinfecting compositions of the present invention are botanical, environmentally sustainable, non-toxic and mildly scented.

25 Claims, No Drawings

ESSENTIAL OILS BASED CLEANING AND DISINFECTING COMPOSITIONS

FIELD OF THE INVENTION

The present invention relates to cleaning and disinfecting compositions, and more particularly to essential oils based compositions for cleaning, disinfecting and sanitizing inanimate and animate surfaces.

BACKGROUND OF THE INVENTION

There is a need for multi-purpose products that function as both effective cleaners and effective disinfectants. Unfortunately, cleaners that demonstrate excellent cleaning performance tend to have poor disinfecting properties, and disinfectants that demonstrate excellent disinfecting performance tend to have poor cleaning properties.

There are a few products that have good cleaning and disinfecting properties. However, these products are typically either heavy duty cleaners and disinfectants for industrial and/or residential use on hard surfaces, or mild antimicrobial cleaners for use on human skin. On the one hand, heavy duty cleaning and disinfecting products generally contain harsh chemicals such as peroxygen bleach, hydrogen peroxide, glutaraldehyde and quaternary ammonium. These chemicals are toxic and poisonous and extreme caution needs to be taken when using cleaners and disinfectants containing these chemicals so as to minimize contact against human skin and damage to surfaces.

On the other hand, cleaning and disinfecting formulas compatible for use on human skin generally do not provide the high cleaning and disinfecting power for targeting microorganisms typically found on hard surfaces, because the porosity and sensitivity of skin makes most hard surface formulations unsuitable. Also, cleaner disinfectants and like products tend to include synthetic chemicals in low concentrations, such as pyrithiones, thiazolinones, sulfites, diazo compounds, chlorinated organics, brominated organics, phenols, bisphenols, resourcinols and alkylated parabens. Even at low concentrations, these chemicals are aggressive, and when the formulation is applied, the dermal oils can be defatted over time. Further, there are concerns that with repeated applications of these cleaner disinfectants, antimicrobial resistance may result due to the presence of synthetic chemicals.

There also exist disinfectant products that do not include toxic chemicals, such as products formulated with naturally occurring essential oils having antimicrobial activity. However, because essential oils are inherently immiscible, essential oils based disinfectants typically utilize a dispersing agent such as a surfactant and/or a solvent to solubilize the essential oils into solution. Although the use of surfactants may improve the stability and shelf life of disinfectants formulated with essential oils, the surfactants tend to hold the essential oils in suspension, in the form of a macro-emulsion, which inhibits the antimicrobial activity of the essential oils.

Many surfactants are also known to be effective cleaning agents. However, surfactants that are good cleaning agents do not necessarily enhance the disinfecting efficacy of the antimicrobial agents. For example, the surfactants utilized in known disinfectants formulated with essential oils, such as the non-toxic biosurfactants disclosed in U.S. Pat. Nos. 6,346,281 and 6,846,498 issued to the present inventor, are not very effective cleaning agents, as they tend to get tied up with the minerals in the hard water used in the cleaning process, which reduces the amount of surfactants available for cleaning. Further, these surfactants have a chemical structure that does not provide optimum surface tension reduction, interfacial surface tension reduction or dispersion properties. For the above reasons, known essential oils based disinfecting compositions are not very effective cleaners. It is also difficult to formulate known essential oils based compositions in concentrated form using naturally-based, biodegradable, non-toxic surfactants, as the surfactants typically are not completely miscible in the oil phase, forming a phase separate from the aqueous components, which makes the compositions unstable and commercially non-viable in the concentrated state.

Accordingly, there is a need for essential oils based cleaning and disinfecting compositions that disperse the essential oils well in a water carrier, and that are stable, have a long shelf life and are affordable and aesthetically appealing to consumers. There is also a need for essential oils based cleaning and disinfecting compositions that are environmentally sustainable, completely botanical or natural, biodegradable, non-toxic, non-streaking, compatible with the human skin, capable of providing shine to inanimate surfaces as well as capable of providing a broad disinfecting spectrum, and that utilize relatively low concentrations of a limited number of naturally occurring essential plant oils. There is further a need for essential oils based cleaning and disinfecting compositions that can be formulated in concentrated form, and thereby sold to end users at an attractive price point and dispensed for dilution at the use site, which is of particular importance for commercial markets where freight costs and storage space are critical, such as the cruise, military and foreign markets.

SUMMARY OF THE INVENTION

The present invention is directed to cleaning and disinfecting compositions for cleaning, disinfecting and sanitizing inanimate and animate surfaces, comprising thyme oil for providing high disinfecting efficacy, sodium dioctyl sulfosuccinate for providing superior cleaning efficacy and microemulsifying properties, and a salt of the transition metal for enhancing the efficiency of the thyme oil. The cleaning and disinfecting compositions of the present invention have been found to be effective not only as heavy duty cleaners but also as disinfectants and as hand sanitizers.

The cleaning and disinfecting compositions of the present invention comprise about 0.01% to about 0.6% by weight of thyme oil, about 0.001% to about 0.10% by weight of a salt of a transition metal, about 0.1% to about 5% by weight of sodium dioctyl sulfosuccinate and sufficient water to make up 100% by weight. These compositions are found to provide surprisingly high cleaning, disinfecting and sanitizing efficacies.

In an embodiment of the present invention, the thyme oil in the cleaning and disinfecting composition is present in an amount of about 0.05% to about 0.15% by weight.

In another embodiment of the present invention, the cleaning and disinfecting composition further comprises about 0.01% to about 0.2% by weight of *origanum* oil, suitably about 0.05% to about 0.1% by weight.

In an embodiment of the invention, the sodium dioctyl sulfosuccinate is present in an amount of about 0.5% to about 2% by weight.

In another embodiment of the invention, the cleaning and disinfecting composition further comprises a second surfactant. Suitably, the cleaning and disinfecting composition comprises about 1% to about 4% by weight of sodium laurel sulphate. More suitably, the cleaning and disinfecting composition comprises about 1.5% to about 2.5% by weight of sodium laurel sulphate.

In yet another embodiment of the present invention, the cleaning and disinfecting composition further comprises about 0.06% to about 1.25% by weight of a buffer. In a particular embodiment, the buffer is a combination of citric acid and sodium citrate. In a more particular embodiment, the citric acid is present in an amount of about 0.01% to about 0.25% by weight and the sodium citrate is present in an amount of about 0.05% to about 1% by weight.

In still another embodiment of the invention, the cleaning and disinfecting composition further comprises about 0.1% to about 1.5% by weight of a degreaser, suitably about 0.3% to about 0.8% by weight. In an embodiment of the invention, the degreaser is selected from D-limonene, pine oil and lemon oil. Suitably, in an embodiment of the invention, the degreaser is D-limonene.

In a more particular embodiment of the present invention, the cleaning and disinfecting composition further comprises about 1% to about 4% by weight of sodium laurel sulphate and about 0.1% to about 1.5% by weight of a degreaser.

In an embodiment of the present invention, the transition metal is selected from copper, iron, zinc and silver. Suitably, in a more particular embodiment of the present invention, the transition metal is copper.

In an embodiment of the present invention, the salt may be a suitable anion. In a more particular embodiment of the invention, the salt is selected from sulfate, chloride, gluconate, hydroxide, nitrate, oxide, octanoate, carbonate, sulfonate, phosphate and phosphonate. More suitably, in an embodiment of the present invention, the salt is sulfate.

Also within the scope of the present invention is a cleaning and disinfecting composition which further comprises an essential oil based fragrance in an amount of about 0.01% to about 0.5% by weight, suitably about 0.05% to about 0.35% by weight. The essential oil based fragrance may be selected from clove oil, lavender oil and citrus oil. Particularly, the citrus oil may be orange, grapefruit, lime, lemon, lemongrass, blood orange, petitgrain and litsea cubeba. More particularly, the citrus oil is litsea cubeba.

In an embodiment of the present invention, the cleaning and disinfecting composition further comprises an emollient. In a more particular embodiment of the invention, the emollient is aloe vera or hydrolyzed protein. In a still more particular embodiment of the invention, the hydrolyzed protein is selected from Cromoist™, Hydroxoy™, and combinations thereof.

The present invention therefore provides for cleaning and disinfecting compositions which have a low level of essential oils and which are environmentally sustainable. The cleaning and disinfecting compositions of the present invention are found to be effective in removing tough grease and stain as well as reducing and eliminating a broad spectrum of microorganisms. The cleaning and disinfecting compositions may be used as a fungicide, virucide, bactericide, germicide or combinations thereof. Also, the cleaning and disinfecting compositions may be used as a hand sanitizer. Since the cleaning and disinfecting compositions comprise substantially natural ingredients which are foods themselves or are listed as Food Additives or Generally Recognized As Safe by the F.D.A. or as minimum risk by the E.P.A., no wiping or rinsing off of the cleaning and disinfecting compositions of the present invention from the surfaces on which the compositions have been applied is required.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

The cleaning and disinfecting compositions of the present invention have high cleaning and degreasing efficacies for removing tough grease and stain as well as high disinfecting and sanitizing efficacies for reducing and eliminating a broad spectrum of microorganisms on a wide variety of surfaces, including both inanimate and animate surfaces. The cleaning and disinfecting compositions of the present invention are environmentally sustainable, completely botanical or natural, biodegradable and non-toxic. The cleaning and disinfecting compositions of the present invention utilize a naturally occurring essential oil, namely thyme oil, at a low concentration level. Thus, unlike typical essential oil based cleaners and disinfectants currently available, the cleaning and disinfecting compositions of the present invention are mildly scented. Further, the cleaning and disinfecting compositions of the present invention are highly stable compositions which may be concentratable such that before application, the consumers can add sufficient water to dilute the compositions. Still further, the cleaning and disinfecting compositions of the present invention preferably utilize water as the sole solvent.

In accordance with an embodiment of the present invention, the cleaning and disinfecting composition comprises:

(a) about 0.01% to about 0.6% by weight of thyme oil;

(b) about 0.001% to about 0.10% by weight of a salt of a transition metal;

(c) about 0.1% to about 5% by weight of sodium dioctyl sulfosuccinate; and (d) sufficient water to make up 100% by weight.

As used herein, the term "concentratable" is understood to mean the pre-consumer dilution and composition of the cleaning and disinfecting composition which is essentially the form of the product prepared for sale to the consumer or other end user. Such a consumer or other end user would then normally be expected to dilute the same with water to form the cleaning and disinfecting composition.

The expressions "environmentally sustainable", "natural", "green" and "botanical" are understood to mean substances or mixtures that are derived from natural sources, whole or substantially all. Thus, these substances or mixtures have minimal environmental impact and require minimal non-renewable inputs when the entire life cycle of the chemical is studied. For example, "natural thymol" refers to thyme oil which is obtained from botanical sources whereas "synthetic thymol" refers to isolated thymol that is chemically synthesized from petroleum.

By "cleaning", it is meant the removal of grease, dirt, soil from inanimate and animate surfaces without leaving films, spots or streaks on the cleaned inanimate and animate surfaces. The term "cleaning" is also understood to mean providing shine to the inanimate surfaces.

By "disinfecting", it is meant the destroying of over 99.99% of selected pathogenic and potentially pathogenic microorganisms, both gram negative and gram positive, on inanimate and animate surfaces within 10 minutes under conditions prescribed by the appropriate government regulatory agency such as the U.S. E.P.A. or Health Canada.

The unregulated term "antibacterial" is used to mean capable of destroying an undefined number of microorganisms, but less then 99.9%, within an undefined period of time. The government regulated term "sanitizer" is used to mean capable of destroying about 99.9% of bacteria in no more than 10 minutes. The government regulated term "fungicidal" is used to mean capable of destroying over 99.99% of selected fungi, particularly *Trichophyton mentagrophytes*, including their spores in no more than 10 minutes. The government regulated term "virucidal" is used to mean capable of destroying over 99.99% of selected viruses in no more than 10 minutes. The term "germicidal" is used to mean capable of destroying pathogenic and potentially pathogenic microorganisms. The term "bactericidal" is used to mean capable of destroying bacteria, but not necessarily bacterial spores or mycobacteria.

In accordance with the present invention, natural essential oils are used in the cleaning and disinfecting compositions. Since these natural essential oils have not been refined or adulterated, they contain non-principal constituents which most likely contribute to the environmental and human health and safety profiles of the compositions, including their antimicrobial properties. As the mechanism of antimicrobial activity is most often unknown for natural essential oils, additional refining beyond the natural whole oil state is anticipated to modify the environmental and health and safety profiles in a negative fashion and possibly promote microbe evolutionary resistance. The thyme oil used in the present invention generally has over 50% thymol and thymol derivatives as well as about 3% to about 7% carvacrol and carvacrol derivatives while the *origanum* oil used in the present invention generally has about 60% carvacrol and carvacrol derivatives as well as about 3% to about 7% thymol and thymol derivatives so as to provide a base level of antimicrobial activities. Representative herbs from which thyme oil may be obtained include *Thymus vulgaris, Thymus serpyllum, Thymus capitatus, Thymus mastichina* and *Thymus zygus*. Representative herbs from which *origanum* oil may be obtained include *Origanum vulgar* and *Origanum dictamnus*. Of course, other herbs from which thyme oil and *origanum* oil or their principal constituents may be obtained are also possible as is readily recognized by persons skilled in the art.

In an embodiment of the present invention, the thyme oil present in the cleaning and disinfecting composition is from about 0.01% to about 0.6% by weight. Suitably, the thyme oil present in the cleaning and disinfecting composition is in an amount of about 0.05% to about 0.15% by weight.

In an embodiment of the present invention, the cleaning and disinfecting composition further comprises about 0.01% to about 0.2% by weight of *origanum* oil, suitably about 0.05% to about 0.1% by weight of *origanum* oil.

Although there exist a great number and different classes of surfactants, including various anionic surfactants, various cationic surfactants, various amphoteric surfactants, as well as various nonionic surfactants, the present inventor has found that the anionic surfactant, sodium dioctyl sulfosuccinate, of the present invention when mixed with the natural essential oils, water and the salt of the transition metal, form a stable macroemulsion or microemulsion of the cleaning and disinfecting composition. In other words, the surfactant, sodium dioctyl sulfosuccinate, acts to help solubilize and disperse the natural essential oils, namely the thyme oil, in the water, making the oils more readily available for antimicrobial activities, ultimately enhancing the disinfecting efficacies of the essential oils and allowing for the use of less oils overall. This not only results in lower production costs, but also in lower fragrance levels. Furthermore, in comparison to existing cleaner disinfectants that commonly contain about 3 to 7% surfactant, the cleaning and disinfecting compositions of the present invention form a stable solution with the use of less than 1% surfactant. Again, this further minimizes the production costs and impact on the environment. At the same time, the use of a low amount of surfactant leads to improved dry-out and wipe profiles. The present inventor also has unexpectedly found that the surfactant, sodium dioctyl sulfosuccinate, of the present invention when combined with the essential oils, salt of the transition metal and water do not compromise its cleaning efficacy but rather maintain its superior cleaning property as well as being an effective stabilizer and an effective solubilizer. The surfactants of the present invention are therefore enhanced dynamic surfactants which can rapidly reduce the surface tension of the water by making it "wetter" so it can spread and wet the inanimate and animate surfaces in the cleaning process and deliver the thyme oil to the microorganisms faster and more completely.

In an embodiment of the present invention, the cleaning and disinfecting composition of the present invention comprises about 0.1% to about 5% by weight of sodium dioctyl sulfosuccinate, more suitably, about 0.5% to about 2% by weight of sodium dioctyl sulfosuccinate. It has been found by the present inventor that the physical properties of this surfactant provide a cleaning and disinfecting composition suitable for use in both the concentrated and end user diluted form. Generally, the sodium dioctyl sulfosuccinate is derived from natural 2-octanol.

In an embodiment of the invention, the cleaning and disinfecting composition further comprises a second surfactant. In a more particular embodiment of the invention, the cleaning and disinfecting composition comprises about 1% to about 4% by weight of sodium laurel sulphate, suitably about 1.5% to about 2.5% by weight of sodium laurel sulphate. The present inventor has found that the combination of the sodium dioctyl sulfosuccinate and sodium laurel sulphate is particularly effective in keeping the tough grease and oily films in suspension, while at the same time, not compromising the disinfecting efficacy of the composition. Due to the short relaxation time of the miscelles for providing rapid mobility and exposure of the oils to the microorganisms, the disinfecting efficacy of the composition is maintained. Further, the advantage of using such surfactants over other types of surfactants is to maintain the benign environmental and human health and safety profiles of the cleaning and disinfecting composition. The sodium dioctyl sulfosuccinate provides enhanced dynamic surface tension and a reduction of the surface tension of water to below 50 dynes/cm at very short surface ages as well. Accordingly, anionic surfactants which have the ability to reduce the surface tension of water to below 50 dynes/cm, when measured at a concentration of 0.5% by weight and a surface age of 100 milliseconds or less are suitable for use with the cleaning and disinfecting composition of the present invention.

A degreaser may also be included in the cleaning and disinfecting composition of the present invention for penetrating and emulsifying grease, oil films and oil-based stains. The degreaser may aid to breakdown heavier soil particles and keep them in suspension, while assuring that the cleaned surfaces remain clean. In an embodiment of the present invention, the degreaser is present in an amount of about 0.1% to about 1.5% by weight, suitably about 0.3% to about 0.8% by weight. The degreaser may be selected from D-limonene, pine oil and lemon oil. In an embodiment of the invention, the degreaser is D-limonene which is a natural solvent extracted from citrus fruit. Thus, it is not only biodegradable and non-toxic, but it also dissolves grease and oil very effectively.

In an embodiment of the present invention, the cleaning and disinfecting composition further comprises about 1% to about 4% by weight of sodium laurel sulphate and about 0.1% to about 1.5% by weight of a degreaser. This combination has been found to be particularly effective as a heavy duty cleaner.

The pH of the composition of the invention may be any pH at which the essential oil microemulsion retains its cleaning, disinfecting and sanitizing efficacies. One of ordinary skill in the art would know the appropriate pHs which are suitable for the composition of the present invention. The pH of the cleaning and disinfecting composition of the present invention ranges from about 0.2 to 10. Specifically, the pH of the cleaning and disinfecting composition ranges from about 3 to 8.

A buffer may be included in the cleaning and disinfecting composition of the present invention to maintain a constant pH of the solution and to serve as a builder to enhance the dispersion properties of the composition. The buffer ties up the hard minerals in water so they do not interfere with the cleaning action of the surfactants. The buffer, in essence, softens water. Furthermore, the buffer aids in keeping the inorganic particles in suspension, assuring that the cleaned surfaces remain clean and preventing the organics from affecting the antimicrobial efficacy. Thus, the present inventor has found that the combination of the buffer, the surfactants, and the degreaser of the present invention, provides the cleaning and disinfecting composition with high degreasing efficacies without interfering with the disinfecting efficacies of the essential oils of the composition. Any known buffer, which is compatible with the components of the composition, may be used. For example, the buffer may be a solution of a weak acid and its salt or a solution of a weak base and its salt. In an embodiment of the present invention, the buffer is about 0.06% to about 1.25% by weight, suitably about 0.25% to about 0.75% by weight. In yet another embodiment of the invention, the buffer is a combination of citric acid and sodium citrate. In a more specific embodiment of the invention, the citric acid is present in an amount of about 0.01% to about 0.25% by weight and the sodium citrate is present in an amount of about 0.05% to about 1% by weight.

The composition of the present invention may include about 0.001% to about 0.10% by weight of the salt of the transition metal. More suitably, in an embodiment of the present invention, the salt of the transition metal in the cleaning and disinfecting composition is about 0.003% to about 0.008% by weight. While not wishing to be limited by theory, it is believed that the inclusion of the salt of the transition metal in the composition catalyzes the disinfecting and sanitizing properties of the thyme oil. The transition metal may be selected from copper, iron, zinc and silver and the salt may be any suitable anions. In an embodiment of the present invention, the salt may be selected from sulfate, chloride, gluconate, hydroxide, nitrate, oxide, octanoate, carbonate, sulfonate, phosphate and phosphonate. Suitably, in an embodiment of the present invention, the salt of the transition metal is copper sulfate.

Water is included as a carrier in an amount sufficient to make the total composition 100% by weight. The water may be tap water, but is preferably distilled and/or deionized water. If the water is tap water, it is preferably appropriately filtered in order to remove any undesirable impurities such as organics or inorganics, especially minerals salts which are present in hard water and which may thus interfere with the operation of the other components of the composition, as well as any other optional components of the composition of the present invention. Water is added in amounts which are sufficient to form the diluted composition which amount is prescribed to ensure the antimicrobial efficacy is achieved.

One or more other ingredients may optionally be included in the cleaning and disinfecting compositions of the present invention to improve the aesthetic or other beneficial properties. Such optional ingredients may include fragrances, emollients, deodorizers, coloring agents, descaling compounds, co-surfactants and the like. These additional ingredients, however, must be compatible with the other core components of the cleaning and disinfecting composition and not negatively affect the environmental as well as the health and safety profiles of the composition of the present invention.

In an embodiment of the invention, the emollient may be aloe vera or hydrolyzed proteins. In a more particular embodiment of the invention, the hydrolyzed protein is selected from Cromoist™, Hydrosoy™, and combinations thereof. With the presence of the emollient, the cleaning and disinfecting composition of the present invention may be used as a hand sanitizer.

The cleaning and disinfecting compositions may further comprise an essential oil based fragrance. Particularly, the essential oil based fragrance is about 0.01% to about 0.5% by weight, suitably about 0.05% to about 0.35% by weight. Representative examples of an essential oil based fragrance which may be compatible with the cleaning and disinfecting composition of the present invention include clove oil, lavender oil and citrus oil. In an embodiment of the invention, the citrus essential oils may be selected from orange, grapefruit, lime, lemon, lemongrass, blood orange, petitgrain and litsea cubeba. In a further embodiment of the invention, the citrus essential oil is litsea cubeba.

Since the components of the cleaning and disinfecting compositions of the present invention originate from herbal essences, in admixture with inert substances, the cleaning and disinfecting compositions of the present invention are readily degradable in the environment and can be used without concern of environmental build up. It has been found that the particular combination of essential oils, namely thyme oil or thyme oil and *origanum* oil, with the salt of the transition metal and sodium dioctyl sulfosuccinate, once dissolved or dispersed in the water, each of which at particular concentration ranges, together exhibits unexpectedly good cleaning property and good disinfecting property against a broad spectrum of microorganisms. The cleaning and disinfecting compositions of the present invention have been found to be surprisingly effective in removing grease, dirt, or soil from inanimate and animate surfaces. Further, the cleaning and disinfecting compositions have been found to be particularly effective in providing shine to inanimate surfaces without leaving films, spots or streaks on the cleaned inanimate surfaces. Still further, the cleaning and disinfecting compositions have been found to be effective against microorganisms, and it is believed that the microorganisms are not expected to develop resistance to the formulations over time.

The cleaning and disinfecting compositions of the present invention may be used as a fungicide, germicide, virucide, bactericide or combinations thereof. Moreover, the cleaning and disinfecting compositions of the present invention may be used as a hand sanitizer. As will be described hereinafter, the cleaning and disinfecting compositions of the present invention have been found to be effective against *Staphylococcus aureus, Escherichia coli, Influenza A virus, Pseudomonas aeruginosa* and *Salmonella choleraesuis.*

Since only natural, food-safe ingredients are included in the cleaning and disinfecting compositions of the present invention, the compositions of the present invention do not need to be wiped off or rinsed off after being applied to the inanimate and animate surfaces. This allows for longer contact with the surface area bearing the microorganisms, and as such ensures a higher killing rate and continuous germ control for extended period of time where desired. Further, since the cleaning and disinfecting compositions of the present invention do not require wiping or rinsing to remove any residues, the cleaning and disinfecting compositions of the present invention are also convenient and easy to use. In addition, the cleaning and disinfecting compositions of the present invention are non-corrosive, non-flammable, non-reactive, readily biodegradable, and have a very low volatile organic compound level of less than 1%.

Still further, it has been found that this particular combination of components provides a stable cleaning and disinfecting composition which can withstand freezing and elevated temperatures. The cleaning and disinfecting compositions of the present invention have been demonstrated to have a shelf life of at least two years.

The cleaning and disinfecting compositions of the present invention may be formulated by conventional procedures known to one skilled in the art. For example, the cleaning and disinfecting compositions can be formulated by combining the essential oils, salt of the transition metal, surfactants, buffer, degreaser and water together. The combined ingredients are then agitated or mixed until a macroemulsified or microemulsified solution of essential oils is formed.

As generally denoted above, the compositions according to the present invention include both diluted and concentrated forms which differ only in the relative proportion of water to that of other components forming the compositions. While the concentrated form of the cleaning and disinfecting compositions of the present invention may be used in their original form for heavy cleaning applications, a prescribed dilution is generally required for disinfection. Such may be easily prepared by diluting measured amounts of the concentrated compositions in water by the consumer or other end user in certain volume ratios of concentrate: water, and optionally agitating the same to ensure even mixing of the concentrate in the water. The compositions may be used at various dilutions for cleaning as well. The actual dilution selected is in part determinable by the degree and amount of dirt and grime to be removed from the surfaces, the amount of scrubbing imparted to remove the same, as well as the observed efficacy of the particular dilution. Generally, better results and faster removal is to be expected at lower relative dilutions of the concentrate in water.

The cleaning and disinfecting compositions of the present invention may be formulated to be dispersed from a ready-to-use dispenser system. For instance, the cleaning and disinfecting compositions may be dispelled from a trigger or finger pump bottle, a squeeze bottle or a pressurized sprayer to produce a spray, fog or foam. The cleaning and disinfecting compositions of the present invention may also be incorporated into a towelette form or a gel or lotion carrier for use to treat a variety of surfaces. The towelettes may be packaged individually or in bulk for individual distribution. Further, the cleaning and disinfecting compositions of the present invention may be incorporated into other formulations or carriers having antimicrobial or disinfecting properties. These formulations may be those of antiseptics, soaps or lotions, dish or laundry soaps, deodorants, toothpastes and air fresheners. Still further, the cleaning and disinfecting compositions of the present invention may be incorporated or impregnated into plastics to preserve the material and provide antimicrobial protection on its surfaces or formulated as a natural preservative into food products, cosmetics or personal care products.

The cleaning and disinfecting compositions contemplated by this invention may be used as a one-step cleaner, disinfectant or sanitizer. The cleaning and disinfecting compositions of the present invention may be used directly on the surfaces to be cleaned, disinfected and sanitized without prior wiping of the surfaces with water to cleanse the surfaces. By way of non-limiting examples, the cleaning and disinfecting compositions contemplated by this invention may be used to clean, disinfect or sanitize human skin surfaces as well as inanimate surfaces such as counters, food preparation surfaces and areas, eating utensils, bathroom fixtures such as sinks and toilets, tiles, floors, walls, windows, furniture, high chair trays, cribs, shopping cart handles, phones, toys, medical instruments and the like. They are also suitable for spraying into residential or commercials air ducts, heating, cooling and ventilation systems.

The following non-limiting examples are illustrative of the invention:

EXPERIMENTAL EXAMPLES

ASTM Standard Guides for Testing Cleaning Performance

Tiles of surface materials such as vinyl, vinyl composite, ceramic, stainless steel were soiled with various types of soils that were particular to specific cleaning applications such as ceramic tile scum, bathroom soil, scale or kitchen grease, and then washed on the Gardner Straight-line washability apparatus. Reflectance values before and after soiling were determined and used to calculate percent of soil removed. Depending on the substrate material used, 10-15 cycles were used on each panel.

AOAC Germicidal Spray Products Test Principle:

A film of bacterial cells dried on a surface of glass slide carriers was exposed to a test substance for a specified contact time. After exposure, the carriers were transferred to vessels containing neutralized subculture media and assayed for survivors. Appropriate viability, carrier population and neutralization confirmation controls were performed. Sixty carriers were tested against each organism, each with 3 samples, and in which one of the samples was at least 60 days old (180 carriers per sample; a total of 540 carriers). Plate count data on appropriate culture media was performed on each test microorganism. It was determined that a concentration of at least $10^4$ microorganisms surviving the carrier-drying step is required. Exposure conditions including growth media, incubation, harvest and drying conditions, including temperature, humidity and amount of spray released from the specified distance from the bacterial films were controlled and recorded. Killing on 59 out of each set of 60 carriers for an effective disinfectant product or 10 out of each set of 10 carriers for a fungicidal product, was used as a standard at a 95% confidence level. A kill was qualitatively determined by visual analysis of turbidity. If the carrier was clear, then total kill of the inoculum load had occurred. Partial kills or nearly total kills would be observed as turbid and therefore a fail.

Time Kill Test Assay for Antimicrobial Agents:

A suspension of bacterial cells was exposed to the test substance for specified contact times. After exposure, an aliquot of the suspension was transferred to a neutralizer and assayed for survivors. Appropriate purity, sterility, microorganism population and neutralization controls were performed. Kill results were expressed quantitatively in log reduction of the test organism within the specified contact time.

The above described methodologies are two examples which may be adapted for testing the efficacies of the cleaning and disinfecting composition as required by governing agencies.

Example 1

Cleaning and disinfecting compositions were prepared, having ingredients of the amount in w/w % specified in Table 1 as follows:

TABLE 1

| | Cleaning and Disinfecting Compositions | | | |
|---|---|---|---|---|
| Components | JS-15 | D50 | D109 | H304 |
| Thyme Oil | 0.1 | 0.5 | 0.1 | 0.1 |
| Fragrance | 0.05 | 0.1 | 0.05 | 0.05 |
| Origanum oil | 0.02 | | 0.02 | 0.02 |
| Sodium Dioctyl Sulfosuccinate | 0.75 | | 1.0 | 0.75 |
| Sodium Laurel Sulphate | | 2.6 | 2.25 | |
| D-Limonene | | | 0.5 | |
| Glucopon | | 5.0 | | |
| Copper Sulfate | 0.004 | 0.002 | 0.004 | 0.07 |
| Citric Acid | 0.03 | | 0.12 | 0.04 |
| Sodium Citrate | 0.07 | | 0.4 | 0.07 |
| Aloe Vera | | | | 0.25 |
| Cromoist ™ | | | | 0.1 |
| Water | to 100% | to 100% | to 100% | to 100% |

Example 2

The cleaning performance of the JS-15, D50 and D109 compositions was determined and the cleaning performance results are shown in Table 2.

TABLE 2

| | % Cleaning Efficiency by Cleaning and Disinfecting Composition | | |
|---|---|---|---|
| Method | JS-15 | D50 | D109 |
| ASTM D4488 A5 Particulate and Oily Soil on Vinyl | 92.60% | | |
| ASTM D4488-A6 Greasy Soil on Vinyl Panels | | 91.88% | 68.50% |
| ASTM D4488-A6 Greasy Soil on Vinyl Composite | | | 40.10% |
| ASTM D5343 Bathroom Soil on Ceramic | | 75.31% | 102.40% |

The data in Table 2 shows that all three of these compositions exhibit cleaning efficacy. In particular, the data shows that with the inclusion of a small amount of sodium dioctyl sulfosuccinate (JS-15 composition of the present invention) or with the inclusion of a small amount of sodium dioctyl sulfosuccinate, a small amount of sodium laurel sulphate, and a small amount of the degreaser D-limonene (D109 composition of the present invention), a superior cleaning efficacy can be achieved than with a composition having a large amount of both sodium laurel sulphate and Glucopon (D50 composition). Thus, it is apparent from the data that with the addition of a small amount of the appropriate surfactant, sodium dioctyl sulfosuccinate, in combination with thyme oil and a salt of a transition metal, an effective cleaning composition can be achieved. The JS-15 composition which is a concentratable formulation has demonstrated to be effective on cleaning particulate and oily soil on vinyl whereas the D109 composition has demonstrated to be effective on cleaning greasy soil on vinyl panels, greasy soil on vinyl composite and bathroom soil on ceramic. The D109 composition has been found to be an effective heavy-duty cleaner.

Example 3

The efficacy of the JS-15, D-50, D109 and H-304 compositions against a variety of bacteria and enveloped viruses was determined and the efficacy results are shown in Table 3.

TABLE 3

| | Kill Results by Cleaning and Disinfecting Compositions | | | |
|---|---|---|---|---|
| Organism: | JS-15 | D50 | D109 | H304 |
| Staphylococcus aureus | >6 log @ 10 min. | 1.09 log @ 10 min. | >5.5 log @ 10 min. | >5 log @ 5 min. |
| Salmonella choleraesuis | >4 log @ 5 min. | | >4 log @ 5 min. | |
| Pseudomonas aeruginosa | >6 log @ 5 min. | | >6 log @ 5 min. | |
| Escherichia coli | >5 log @ 5 min. | | >5 log @ 5 min. | |
| Rhinovirus Type 37 | >5.5 log @ 10 min. | | | |
| Influenza A | >7 log @ 5 min. | | >7 log @ 5 min. | |

To be considered as a highly effective cleaning and disinfecting composition, an antimicrobial reduction greater than 4 log is generally required. It can be seen from the data in Table 3 that the cleaning and disinfecting compositions JS-15, D109 and H304 of the present invention are the most effective compositions from the group of cleaning and disinfecting compositions tested. Thus, in comparison with the D50 composition, the inclusion of a small amount of *origanum* oil in combination with a small amount of the appropriate surfactant, that is sodium dioctyl sulfosuccinate, in the concentratable JS-15 composition of the present invention and the hand sanitizer H304 composition of the present invention or with the surfactant combination sodium dioctyl sulfosuccinate and sodium laurel sulphate as well as the degreaser D-limonene in the heavy duty cleaner composition of D109, a much superior disinfecting efficacy can be achieved. Furthermore, it can be seen from the data in Table 3 that with the inclusion of an emollient in the composition H304, the disinfecting efficacy of the hand sanitizer H304 is on par with those of the JS-15 and D109 compositions of the present invention.

Example 4

The storage stability of the cleaning and disinfecting composition JS-15 was determined using an accelerated method that simulates 2 years of storage by exposing the composition to 54° C. for 14 days. Conclusion of the study was that the composition was stable.

TABLE 4

| | % Thymol Present in Composition | | |
|---|---|---|---|
| Method | Standard | Initial | 14 Days |
| OPPTS 830.6317 Accelerated Storage Stability | 0.045-0.055% | 0.051% +/- 0.001% | 0.048% +/- 0.001% |

I claim:

1. A cleaning and disinfecting composition comprising:
   (a) about 0.01% to about 0.6% by weight of thyme oil;
   (b) about 0.001% to about 0.10% by weight of a salt of a transition metal;

(c) about 0.1% to about 5% by weight of sodium dioctyl sulfosuccinate; and (d) sufficient water to make up 100% by weight.

2. The cleaning and disinfecting composition according to claim 1, further comprising about 0.01% to about 0.2% by weight of *origanum* oil.

3. The cleaning and disinfecting composition according to claim 2, wherein the *origanum* oil is present in an amount of about 0.05% to about 0.1% by weight.

4. The cleaning and disinfecting composition according to claim 1, further comprising about 0.06% to about 1.25% by weight of a buffer.

5. The cleaning and disinfecting composition according to claim 4, wherein the buffer is a combination of citric acid and sodium citrate.

6. The cleaning and disinfecting composition according to claim 5, wherein the citric acid is present in an amount of about 0.01% to about 0.25% by weight and the sodium citrate is present in an amount of about 0.05% to about 1% by weight.

7. The cleaning and disinfecting composition according to claim 1, further comprising about 1% to about 4% by weight of sodium laurel sulphate.

8. The cleaning and disinfecting composition according to claim 7, wherein sodium laurel sulphate is present in an amount of about 1.5% to about 2.5% by weight.

9. The cleaning and disinfecting composition according to claim 1, further comprising about 0.1% to about 1.5% by weight of a degreaser.

10. The cleaning and disinfecting composition according to claim 7, further comprising about 0.1% to about 1.5% by weight of a degreaser.

11. The cleaning and disinfecting composition according to claim 9, wherein the degreaser is selected from the group consisting of D-limonene, pine oil and lemon oil.

12. The cleaning and disinfecting composition according to claim 11, wherein the degreaser is D-limonene.

13. The cleaning and disinfecting composition according to claim 1, wherein sodium dioctyl sulfosuccinate is present in an amount of about 0.5% to about 2% by weight.

14. The cleaning and disinfecting composition according to claim 1, wherein the thyme oil is present in an amount of about 0.05% to about 0.15% by weight.

15. The cleaning and disinfecting composition according to claim 1, wherein the transition metal is selected from the group consisting of copper, iron, zinc and silver.

16. The cleaning and disinfecting composition according to claim 1, wherein the salt is selected from the group consisting of sulfate, chloride, gluconate, hydroxide, nitrate, oxide, octanoate, carbonate, sulfonate, phosphate and phosphonate.

17. The cleaning and disinfecting composition according to claim 1, wherein the salt of the transition metal is copper sulfate.

18. The cleaning and disinfecting composition according to claim 1, further comprising about 0.01% to about 0.5% by weight of an essential oil based fragrance wherein the essential oil is different from the thyme oil.

19. The cleaning and disinfecting composition according to claim 18, wherein the essential oil based fragrance is present in an amount of about 0.05% to about 0.35% by weight.

20. The cleaning and disinfecting composition according to claim 18, wherein the essential oil based fragrance is selected from the group consisting of clove oil, lavender oil and citrus oil.

21. The cleaning and disinfecting composition according to claim 20, wherein the citrus oil is litsea cubeba.

22. The cleaning and disinfecting composition according to claim 1, wherein the cleaning and disinfecting composition is used as a fungicide, germicide, virucide, bactericide or combinations thereof.

23. The cleaning and disinfecting composition according to claim 1, further comprising an emollient, and wherein the cleaning and disinfecting composition is used as a hand sanitizer.

24. The cleaning and disinfecting composition according to claim 23, wherein the emollient is selected from the group consisting of aloe vera and hydrolyzed protein.

25. The cleaning and disinfecting composition according to claim 24, wherein the hydrolyzed protein is selected from the group consisting of Cromoist™, Hydroxoy™, and combinations thereof.

* * * * *

UNITED STATES PATENT AND TRADEMARK OFFICE
Certificate

Patent No. 7,465,697 B1

Patented: December 16, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: S. Samuel DeAth, Waterdown (CA); and Larry Weiss, M.D., San Francisco, CA (US).

Signed and Sealed this Fifteenth Day of March 2011.

HAROLD Y. PYON
*Supervisory Patent Examiner*
Art Unit 1761
Technology Center 1700